US005923259A

United States Patent [19]

Lederer

[11] Patent Number: 5,923,259

[45] Date of Patent: Jul. 13, 1999

[54] LEAK DETECTION ALARM WITH "STETHOSCOPE" SPRING CONTACTS

[76] Inventor: Gabor Lederer, 28 Summit Ave., Hackensack, N.J. 07601

[21] Appl. No.: 08/885,640

[22] Filed: Jun. 30, 1997

Related U.S. Application Data

[63] Continuation of application No. 08/755,282, Nov. 22, 1996, abandoned.

[51] Int. Cl.$^6$ .......... G08B 21/00

[52] U.S. Cl. .......... 340/605; 340/573.1; 340/604; 324/693; 606/34

[58] Field of Search .......... 340/604, 605, 340/540, 573.1; 324/556, 557, 693, 694; 73/40, 45.5; 606/34

[56] References Cited

U.S. PATENT DOCUMENTS

| | | | |
|---|---|---|---|
| 4,909,069 | 3/1990 | Albin et al. | 340/605 |
| 4,956,635 | 9/1990 | Langdon | 340/540 |
| 5,036,309 | 7/1991 | Dennison, Jr. | 340/540 |
| 5,351,008 | 9/1994 | Leach et al. | 340/605 |
| 5,430,434 | 7/1995 | Lederer et al. | 340/540 |
| 5,600,250 | 2/1997 | Thompson | 340/540 |
| 5,658,277 | 8/1997 | Marshall et al. | 340/540 |

*Primary Examiner*—Daniel J. Wu
*Attorney, Agent, or Firm*—Israel Nissenbaum

[57] ABSTRACT

An electrically powered integrity checking device for detection of breaches in protective garments under conditions of a potential for exposure to any one of bodily fluids and hazardous fluid materials. The device comprises a connector for electrically connecting a person wearing a protective garment to the device and a second connector to a fluid source. The device comprises a current source, an alarm, with constant monitoring of integrity of each connection during use of the device. A breach in the protective garment allows ingress of fluid through the breach, results in a completed circuit from the current source means, between the person wearing the protective garment and the fluid source, which triggers said alarm. The connector comprises a reusable spring loaded clamping structure which maintains pressure terminal contact with the person.

3 Claims, 2 Drawing Sheets

LEAK DETECTION ALARM WITH "STETHOSCOPE" SPRING CONTACTS

FIELD OF THE INVENTION

This is a continuation of U.S. application Ser. No. 08/755,282, filed Nov. 22, 1996, now abandoned. This invention relates to alarm detectors used for testing and warning of breakage in protective gloves, particularly those worn during surgery and in laboratory environments, prior to and during use and to connective elements used therewith.

BACKGROUND OF THE INVENTION

Surgical and laboratory procedures are fraught with the possibility of infectious contact of surgical and laboratory personnel with body fluids, particularly the blood of patients and of test specimens. Surgical gowns and gloves are designed to provide protection. However, exigencies of the situation, particularly with the use of sharp instruments, contact with bone, application of excessive pressure and necessarily thin gloves can occasionally lead to unnoticed pinholes, rips, etc. in the protective garment. This leads to the ingress of possibly infectious body fluids into direct contact with the surgical personnel. The prevalence of AIDS and HIV has most recently exacerbated such concern. Accordingly, devices have been utilized during surgery to warn surgical personal of breakages and breaches in protective garments worn during surgery, in order to minimize the extent of exposure to contaminated fluids and the transmission of bacteria or viral pathogens. Expedients to alleviate such concern generally encompass the use of pin-hole detection devices which provide immediate warning of even small breaches to allow for immediate effective action.

An example of such warning device is disclosed in U.S. Pat. No. 4,956,635 in which a circuit, interrupted by the surgical gloves, is established between surgeon and patient. A reference external electrical circuit is established on the surgeon, wherein a breach in the glove barrier results in a measurable voltage drop which triggers an alarm warning. However, spurious signals can be triggered, such as by static electric charge build-ups and discharges, which generate a sufficient voltage. Interruptions in surgical procedures resulting from spurious signals are costly and possibly harmful.

In my prior U.S. Pat. No. 5,430,434, the disclosure of which is incorporated herein, by reference thereto, an alarm device was described for use in detection of a breach in at least one protective barrier between an object and at least one carrier, during surgical and health care procedures but with contained means for minimizing spurious alarms. The device is separately electrically connected, with individual connections to the object and at least one carrier, said device comprising alarm means, central processing means, and means to constantly monitor integrity of each connection during use of the device. Any failed connection condition causes the alarm means to generate an alarm as to such condition to enable the failed connection condition to be corrected. With a breach in the protective barrier, and establishment of a conductive connection between the object and one carrier, a circuit is completed through the device with a current generation, and a warning alarm is triggered by the alarm means. The device further having discrimination means wherein said alarm is only triggered when the discrimination means determines that the generated current is of a specific predetermined type.

The device described in said patent is portable or use in detection of breaches in protective garments such as gloves, during surgical procedures and the like. The device is electrically connected to an object (e.g. patient) and one or more carriers (e.g. a surgeon and/or health care workers) and comprises electrical pulse generation means and central processing means whereby electrical pulses, continually generated by the electrical pulse generation means, are separately directed to the surgeon and the patient, to monitor integrity of each connection during use of the device. A failed connection provides an alarm as to such condition to enable it to be corrected. With a barrier breakdown, such as a hole in a surgical glove, and establishment of a conductive fluid connection with in vivo patient fluids, such as blood (of a possibly hazardous nature), a circuit is completed between the surgeon and patient, and through the device, and a warning alarm is triggered. Such alarm is however only triggered when the central processing means determines that a generated current is of a pulse type and is of the specific pulse rate generated by the pulse generation means. The pulse generations for each of patient and surgeon are preferably identical but phase shifted so that they are separately identifiable. With the completion of the circuit between surgeon and patient, the pulses are shunted to the breach alarm circuit and combined. It is this combined pulse rate which is detected and analyzed by the central processing means.

The pulse generation and rate detection eliminates any spurious signals with unwanted alarm triggering. The device senses only the presence or absence of the pre-established signal and is analogous to a switch being open and closed. Secondary source changes in resistance levels, as is possible with prior art devices, are not a factor in alarm triggering. Such alarm may be in the form of visual, audio or tactile indications, e.g. a blinking warning light, a sounding buzzer or beep, or a detectable vibratory movement. In a preferred embodiment, means are provided for a remote perception of the alarm near the surgeon's eyes or ears. Separate alarm indicators inform the user of low battery condition and loss of connection integrity from either the surgeon or patient connection.

In an embodiment of the device, the device embodies a central processor and source unit containing sensing wave or pulse generator, indicators, driving circuitries, digital analyzing and monitoring circuitries and a power source. The device is separately directly connected to the object, e.g. skin of the patient, and to the device carrier, e.g. skin of the surgeon, via standard two conductor wires and EKG type dual electrodes. The driving and monitoring circuitries, which generates a pulse specific current, prevents spurious signals despite the heightened sensitivity required by the device for triggering and the presence of numerous electronic devices, with emitting electrical discharges, which are present in operating rooms. The device is provided with self diagnostic monitoring means to ensure proper over-all hook-up; separate proper connection to each of the surgeon and patient; sufficient battery power; and proper operation.

In all such prior devices electrical contact is made with the surgeon's (and patients) or other workers' skin by means of disposable adhesively attached leads. These leads require time and effort to adhere, are not safely reusable and because of the adhesive used, are uncomfortable and possibly painful to utilize and remove and may be difficult to be properly located for a good electrical contact.

SUMMARY OF THE INVENTION

It is an object of the present invention to provide a combination pre-utilization and during utilization, diagnostic device for checking the integrity of protective gloves used in medical, dental and laboratory environments.

It is a further object of the present invention to provide such device with a reusable spring loaded electrical connector, which is sterilizable and reusable and is fast and easy to position and remove.

It is a still further object of the present invention to provide such connector in the form of a stethoscope having a self checking configuration to constantly monitor integrity of the electrical connection.

These and other objects, features and advantages of the present invention will become more evident from the following discussion and the drawings in which.

DETAILED DESCRIPTION OF THE INVENTION

Figure 1:
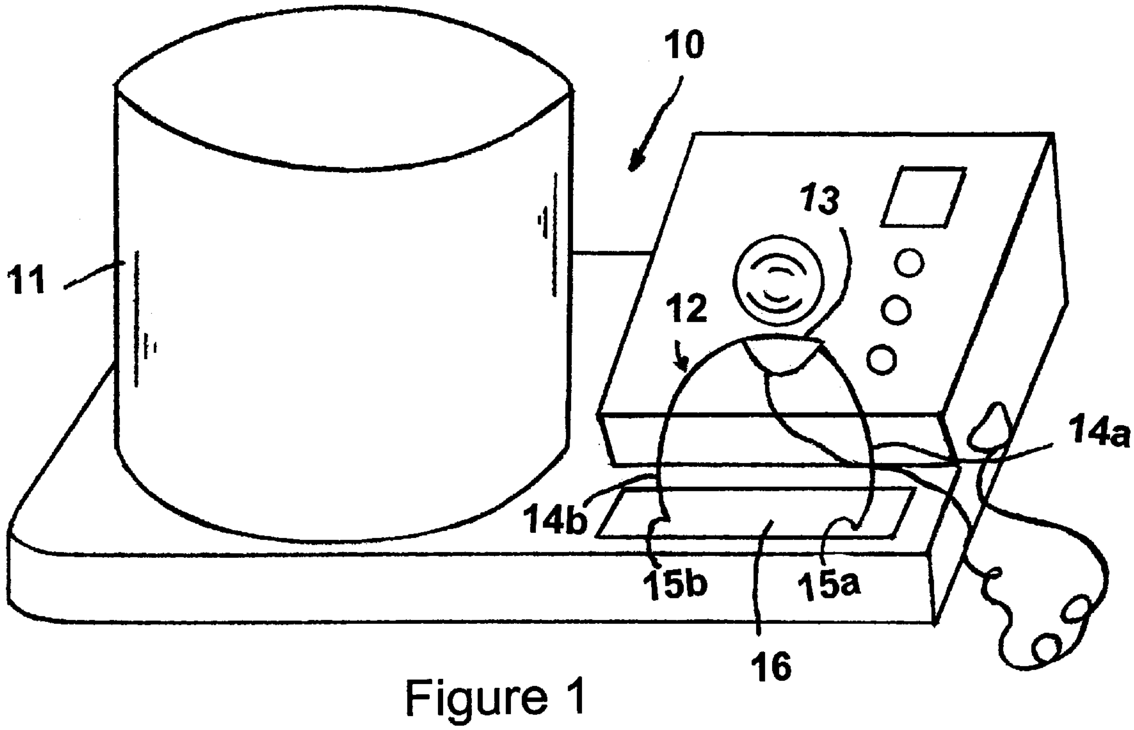
FIG. 1 is a schematic depiction of the device of the present invention.

The present invention comprises an integrity checking device for detection of breaches in protective garments, such as gloves made of perforable material such as latex, used by laboratory technicians during laboratory procedures or other testing procedures in medicine or dentistry where there is a potential for exposure to bodily fluids and other hazardous and potentially hazardous materials. For power and as a source for the current used in the detection, the device of the present invention utilizes either a battery or a 110v wall transformer which provides real-time digital surveillance testing of the integrity of protective glove barriers.

The electrically powered integrity checking device provides detection of breaches in protective garments under conditions of a potential for exposure to bodily fluids and hazardous fluid materials. The device comprises first connection means for electrically connecting a person wearing a protective garment to the device and second connection means for connection to a fluid source which can either be a patient having body fluids or a tank with a testing fluid. The device further comprises current source means, alarm means, and means to constantly monitor integrity of each connection during use of the device. When a breach in the protective garment allows ingress of fluid through the breach, the result is the completion of a circuit from the current source means, between the person wearing the protective garment and the fluid source. Completion of the circuit triggers the alarm means.

In accordance with the present invention, the connection to the person comprises reusable spring loaded clamping means with a pressure connection which maintains terminal contact of the connection means with the person.

The device indicates the alarm condition by means of a sound and/or a flash of light such as a red light upon any direct fluid contact, which may occur through a microscopic hole in a protective glove, as is most commonly worn by medical, dental and laboratory workers.

The device is electrically attached to the skin of the surgeon and patient with the spring loaded connection means, for completion of an electrical circuit upon breach of the glove or only to the skin of the worker in a laboratory or other similar medical or dental environment. In accordance with the present invention and to facilitate utilization of the device, electrical connection is effected by spring loaded connector means which gently but firmly clamps to the skin, without need to use an adhesive connection. The connector means are reusable and the device preferably also includes a sterilizing trough into which the connector leads are placed between uses for the dual purpose of sterilization and to maintain contact elements in a moist condition to enhance electrical connection.

In a preferred embodiment, the device comprises a portable counter-top sealed unit having an attached stainless steel spring loaded "stethoscope" shaped connected electrically attached thereto, and a stainless steel tank which holds a saline test fluid and a separate sterilizing bath trough.

In one means of utilization, when properly connected and activated, the device continuously performs an integrity test of the protective gloves worn by a worker during any laboratory or testing procedure in medicine or dentistry. The unit alerts workers immediately upon detection of a defect in the protective barrier which may occur at any time, thereby signaling the worker to change gloves or to take other appropriate measures.

In another embodiment, involving initial checking of the integrity of the glove, electrical contact is made between the device, which generates a current (pulsed for greatest discrimination efficiency) and the skin of the worker wearing the glove. The exterior surface of the glove is placed into electrical contact with the device, i.e., another part of the circuit from which the electrical charge is directed to the worker. A breach in the glove completes the circuit thereby activating an alarm which warns the wearer of a breach.

In addition to the alarm effected with completion of the circuit, the device also comprises continuous self diagnostic testing means which consists of an internal check of the electronic functions and the integrity of its connection. If any of the elements of the tank or stethoscope connector are detached, the unit will sound and flash a different alarm (at a low level) and will stay on until the connection is reestablished or the unit is turned off.

In an example of an operative warning system, in the event of a low battery condition, a flashing light (e.g., a flashing yellow light) is activated as an indication for the need for battery replacement. A flashing light of a different color, e.g., red, may be made to be indicative of an alarm condition, which with a sound alarm, is utilized to alert the worker of a possible danger from pathogen transmission. A flashing green light indicates a normal "stand by" condition and operation of the unit.

In operation, the device is connected to the protected worker via the reusable contact electrode in the form of a spring loaded "stethoscope" and the contact electrode is "clipped" thereby to the skin on the worker. The "horns" of the stethoscope are preferably electrically isolated from one another whereby they can be independently constantly monitored for integrity of the connection and circuit arrangement. The device comprises digital surveillance circuitry which discriminates the resistive and capacitive differences between defective (punctured) and non-defective gloves. If a hole or permeability exists in the glove during a test procedure for testing the glove, the circuitry transmits the signal difference via the electrode and tethering device and an alarm is sounded. The device is capable of detecting holes from 1.5 microns in diameter, with a response time of less than 15 microseconds. After use, the contact electrode is unclipped and the contact elements are immersed in a sterilizing bath trough.

DESCRIPTION OF THE DRAWINGS AND EMBODIMENT

Figure 2:
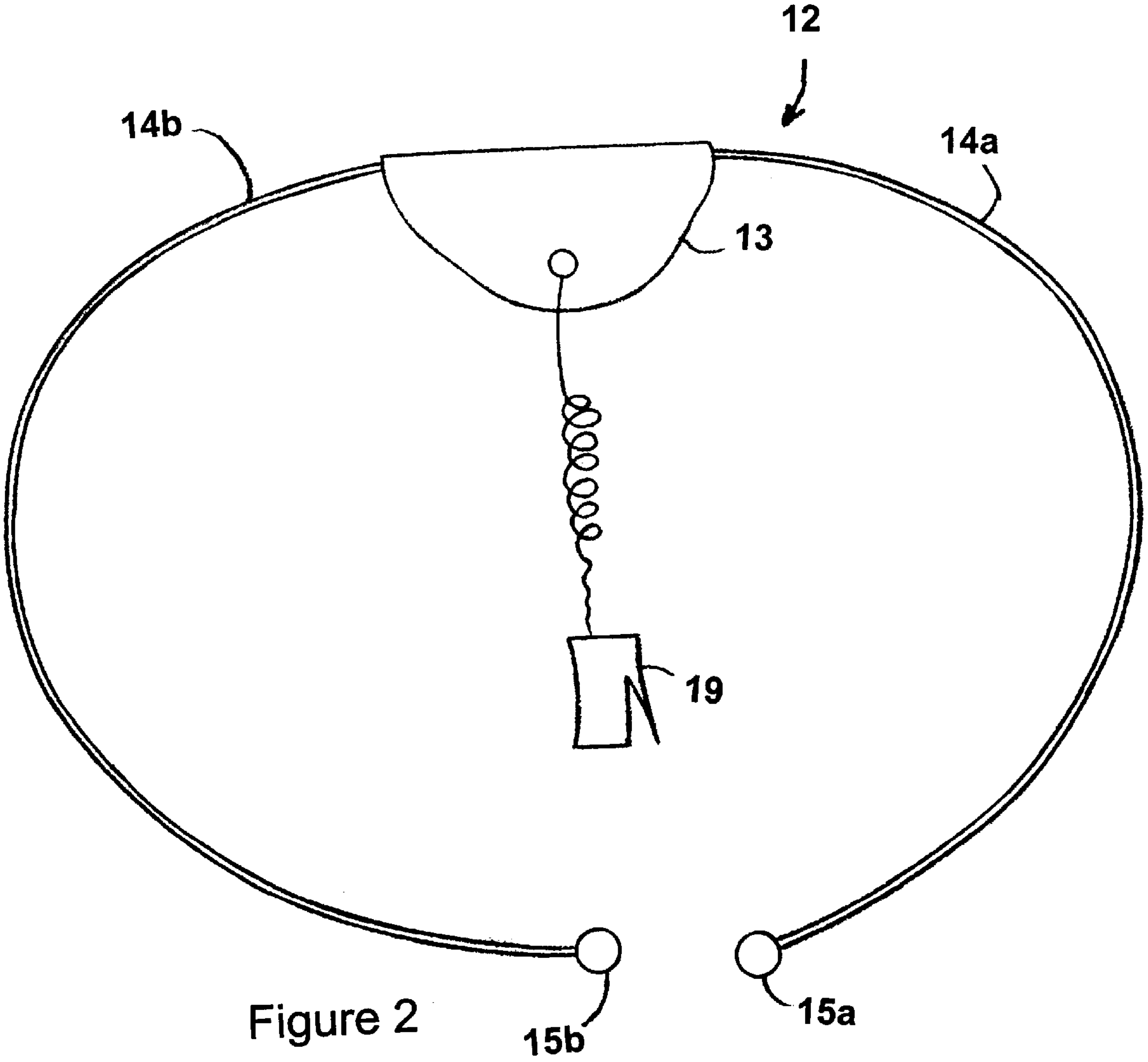
FIG. 2 depicts the spring loaded connector used in the device of FIG. 1.
Figure 3:
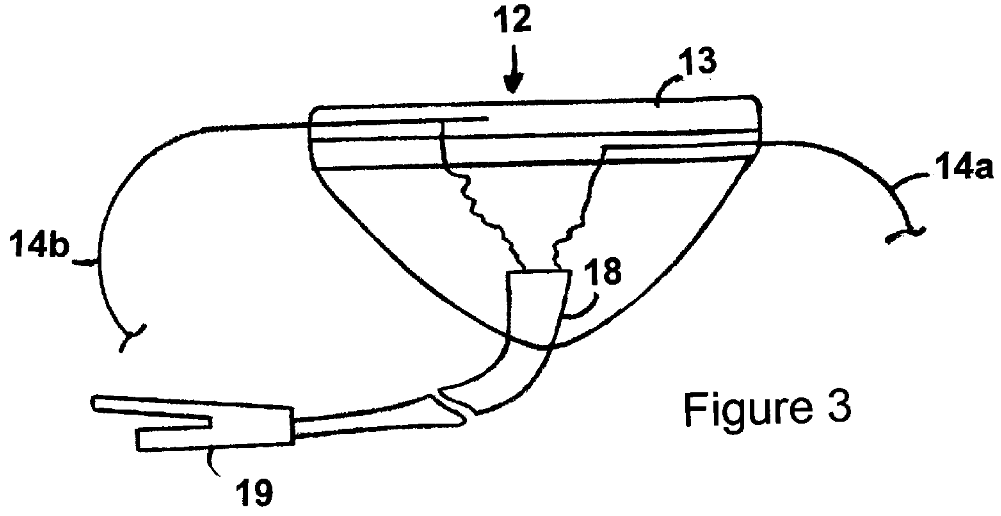
FIG. 3 is a view of the spring loaded connector with a wall of the horn holder removed to show the internal connections.

The test procedure involves testing of a glove in tank container 11 of device 10, shown in FIG. 1, in which there is an ion containing liquid (e.g. a saline solution) conducting solution by sticking the glove covered hand into the liquid solution. The tank 11 is connected to an electronics surveillance circuitry, similar to that disclosed in my prior patent, wherein the device issues modulated or direct electrical signals to the liquid via wiring in electrical contact with the liquid. The other output is connected to the protected person's skin via stethoscope electrode 12, shown in more detail in FIGS. 2 and 3, comprised of a central insulative retaining element 13 and curved right and left horns 14*a* and 14*b* horns which terminate in contact pads 15*a* and 15*b* respectively. The contact electrode 12 is electrically connected to the alarm device 10, via extendible lead 18 and plug 19. As seen in FIG. 3, the right and left horns are electrically separated and are connected via two conductors in lead 18, whereby the integrity of each can be constantly checked by the device 10.

The contact pads 15*a* and 15*b* are normally closely adjacent and are spring buttressed against retaining element 13 via the respective metal (stainless steel) horns (held in separate channels in retaining element 13), whereby they are readily clamped to the user's skin. Trough 16 contains a liquid, preferably sterilizing, into which the contact pads 15*a* and 15*b* are immersed between uses.

For quick and effective laboratory, use a worker dons a protective glove, clamps the contact pads against his skin, such as on the forearm above the area of the hand, and immerses only the glove into tank 11 containing the electrically conductive fluid (care should be taken to insure that the hand above the glove is not in contact with the solution. If the glove barrier is defective the signal will be received through the skin contact by the device and a warning signal will be sounded or made visible and the glove is discarded and another one donned and tested. Because of the ease in effecting connection and disconnection, periodic inspections of the integrity of the glove are readily made at any time or with any doubt regarding a possible breach which may not even be visible.

It is understood that changes in structure and components are possible in keeping with the present invention and that the above description and drawings are merely exemplary of the present invention.

What is claimed is:

1. An electrically powered integrity checking device for detection of breaches in protective garments under conditions of a potential for exposure to any one of bodily fluids and hazardous fluid materials, said device comprising first connection means for electrically connecting a person wearing a protective garment to the device and second connection means to a fluid source, said device comprising current source means, alarm means, and means to constantly monitor integrity of each connection during use of the device and wherein a breach in the protective garment allowing ingress of fluid though the breach results in a completed circuit from the current source means, between the person wearing the protective garment and the fluid source, which triggers said alarm means, wherein the first connection means comprises reusable spring loaded clamping means to maintain terminal contact of the connection means with the person, wherein the spring loaded clamping means comprises two opposingly positioned, resilient horns, each having one end fixed within a non-conducting based element and another conductive terminal end adapted to effect clamping of skin of the person between the terminal ends of the horns, with each of the horns comprising conductive means for completion of said circuit and wherein each of the horns is electrically isolated form the other whereby integrity of an electrical connection to one of the horns is monitorable apart from the integrity of an electrical connection to the other of the horns.

2. The device of claim 1, wherein the fluid source is a fluid tank element electrically connected to the current source means and containing a conductive fluid and wherein the protective garment is a glove which is dipped in the conductive fluid while being worn on a hand of the person, for the checking of the integrity thereof.

3. The device of claim 2, wherein the device further comprises an electrolytic fluid reservoir for insertion of the conductive terminal ends of the horns for maintaining said terminal ends conductively moist during storage thereof.

* * * * *